United States Patent [19]

Irnich

[11] Patent Number: 4,856,521

[45] Date of Patent: Aug. 15, 1989

[54] CARDIAC PACEMAKER HAVING A VARIABLE STIMULATION FREQUENCY

[76] Inventor: Werner Irnich, Birkenweg 60, 6301 Wettenberg 3, Fed. Rep. of Germany

[21] Appl. No.: 78,049

[22] Filed: Jul. 27, 1987

[30] Foreign Application Priority Data

Jul. 31, 1986 [DE] Fed. Rep. of Germany ....... 3625894

[51] Int. Cl.$^4$ .......................... A61N 1/00; H05G 00/00
[52] U.S. Cl. .............................................. 128/419 PG
[58] Field of Search ....... 128/419 P, 419 PG, 419 PS, 128/419 PT

[56] References Cited

U.S. PATENT DOCUMENTS

| | | | |
|---|---|---|---|
| 4,060,090 | 11/1977 | Lin et al. ...................... | 128/419 PG |
| 4,108,148 | 8/1978 | Cannon, III ................. | 128/419 PG |
| 4,228,803 | 10/1980 | Rickards ...................... | 128/419 PG |
| 4,527,568 | 7/1985 | Rickards ...................... | 128/419 PG |
| 4,590,944 | 5/1986 | Mann et al. ................. | 128/419 PG |
| 4,624,260 | 11/1986 | Baker, Jr. et al. ........... | 128/419 PG |
| 4,712,555 | 12/1987 | Thornander et al. ........ | 128/419 PG |

FOREIGN PATENT DOCUMENTS 8605698 10/1986 PCT Int'l Appl. .......... 128/419 PG

OTHER PUBLICATIONS

"Stimulation sequentielle et delai auriculo–ventriculaire optimal", J. C. Daubert, Ph. Ritter, Ph. Mabo, Stimucoeur T. 14, No. 2.
"Bifocal Demand Pacemaker", Barouh V. Berkovits, et al. Abstracts of the 42nd Scientific Sessions, Suppl. III to Circ. vol. XXXIX and XL Oct. 1969.
"The ideal Pacemaker", Werner Irnich, Offprint from Boston Colloquium on Cardiac Pacing, Martinus Nijhoff Medical Division, The Netherlands.
H. D. Funke et al. (1982) "VSAP: A Cardiac Pacemaker with Automatic Adapation of the Atrial Stimulation Rate", in Cardiac Pacing, G. A. Feruglio Ed., Piccin Medical Books, Padova, 1235–1238.

Primary Examiner—Francis Jaworski
Assistant Examiner—George Manuel
Attorney, Agent, or Firm—Marmorek, Guttman & Rubenstein

[57] ABSTRACT

A cardiac pacemaker includes a stimulation electrode connected to the atrium and a pulse generator coupled to the stimulation electrode and operable for producing electrical pulses at a selectable frequency. A monitoring electrode is connected to the ventricle and is operable for sensing excitation signals in the ventricle in response to the electrical pulses at the stimulation electrode. The timing means is coupled to both the pulse generator and the monitoring electrode and is operable for measuring the time interval between an electrical pulse at the stimulation electrode and the occurrence of the associated excitation signal. An evaluation means is coupled to the timing means and is operable for evaluating the time interval. The evaluation means is coupled to the pulse generator and is operable to change the frequency of said pulse generator.

6 Claims, 4 Drawing Sheets

CARDIAC PACEMAKER HAVING A VARIABLE STIMULATION FREQUENCY

VIEW OF THE INVENTION

The invention relates to a cardiac pacemaker and particularly to a cardiac pacemaker which can evaluate an intracardial electrical signal and adjust the stimulation frequency of the cardiac pacemaker according to predetermined criteria.

BACKGROUND OF THE INVENTION

Generally, cardiac pacemakers have been used for many years to provide stimulation to a heart in order to regulate the pumping rate of the heart. The stimulation is in the form of electrical pulse signals. Cardiac pacemakers are available for providing a variable frequency of electrical pulse signals depending upon the requirements of the circulatory system. As used herein, the operating frequency of a cardiac pacemaker will be referred to as the "stimulation frequency".

Generally, the stimulation frequency of such cardiac pacemakers is relatively low when the body is at rest and increases in accordance with the stresses experienced by the body up to a predetermined maximum stimulation frequency predetermined for each individual case. Such variable frequency cardiac pacemakers utilize a sensing system for evaluating the degree of stress on the circulatory system to vary the stimulation frequency.

U.S. Pat. No. 4,228,803 discloses a variable stimulation frequency cardiac pacemaker in which the ventricle of the heart is stimulated. The stimulation electrode is located within the ventricle and also serves as a sensor. The cardiac pacemaker utilizes the well known fact that the time interval defined in an EKG between the Q peak and the T wave becomes shorter as body stress increases. In this cardiac pacemaker, the time interval between a stimulation electrical pulse and the following T wave is measured in a timing circuit and an evaluation circuit controls the frequency of the sequence of stimulation electrical pulses as a function of the measured time interval. This is referred to in the art as the "stimulus T principle".

The cardiac pacemaker disclosed in the '083 Patent can only be used in the ventricle and is not suitable at all for the atrium of the heart because there is no electrical signal corresponding to the T wave detectable in the atrium. This has the drawback that this cardiac pacemaker cannot be used with patients suffering from an excitation-producing or excitation-transmitting disease limited to the atrium. This is because no physiological synchronization will occur between the atrium and ventricle for such patients using this cardiac pacemaker.

In addition, it is possible that for such patients the stimulation of the ventricle could lead to a retrograde excitation of the atrium which usually results in a contraction of the atrium against the closed heart valve. This condition results in the physiological disadvantage of blood being pumped back into the veins rather than being pumped from the atrium into the main chamber of the heart.

U.S. Pat. No. 4,527,568 discloses a variable frequency cardiac pacemaker which utilizes the time interval between the stimulation electrical pulses and the T wave as a control value in a control circuit to control the stimulation frequency. This cardiac pacemaker combines an atrial-controlled ventricle pacemaker using the stimulus T principle. This cardiac pacemaker includes an additional sensor to provide an additional parameter related to the state of stress. The parameter can be pH value, the venous oxygen content, the body temperature, or the breathing velocity. This cardiac pacemaker can be used with patients suffering from an atrioventricular block (AV-block).

U.S. Pat. No. 4,108,148 discloses a cardiac pacemaker in which the ventricle is subjected to stimulation electrical pulses and the control of the operation is based on an electrical signal detected in the atrium of the heart. As used herein, the electrical signal in the atrium will be referred to as the "excitation signal". The operation of this cardiac pacemaker is related to the atrium-ventricle interchange time. As used herein, the atrium-ventricle interchange time is referred to as the "$T_{AR}$". The atrium-ventricle interchange time is often referred to as the "AR-interval".

The operation of the cardiac pacemaker disclosed in the '148 Patent assumes that the $T_{AR}$ is not constant with a functioning atrium-ventricle interchange and that it changes as a function of the stimulation frequency. In particular, it is assumed that $T_{AR}$ is relatively long for a relatively low stimulation frequency and relatively short for a relatively high stimulation frequency. The operation of the cardiac pacemaker adjusts the natural functioning of the heart by taking into account the shortening of the atrium-ventricle interval time when sensing a higher frequency of the autonomous atrial activity in response to ventricle stimulation.

U.S. Pat. No. 4,060,090 discloses a cardiac pacemaker in which the atrium-ventricle interval depends upon the stimulation frequency and becomes shorter as the stimulation frequency increases. This cardiac pacemaker utilizes this information for the stimulation of the ventricle.

The present invention provides a cardiac pacemaker which takes into account body stress by relatively simple and reliable measurements and is suitable for use with patients having excitation-producing or excitation-transmitting disease of the atrium.

SUMMARY OF THE INVENTION

The invention relates to a cardiac pacemaker having a variable stimulation frequency. The cardiac pacemaker is connected to the atrium and the ventricle. A stimulation electrode is connected to the atrium and a pulse generator is coupled to the stimulation electrode to provide electrical pulses at a selectable stimulation frequency. A monitoring electrode is connected to the ventricle and senses excitation signals in response to the electrical pulses at the stimulation electrode.

Timing means is coupled to both the pulse generator and the monitoring electrode for measuring the time interval between an electrical pulse at the stimulation electrode in the atrium and the associated excitation signal in the ventricle. An evaluation means is coupled to the timing means and evaluates the measured time interval. The evaluation means can change the operating stimulation frequency of the pulse generator based on the measured time interval.

The invention utilizes a newly-discovered phenomena. It is known that the AR-interval becomes shorter during a natural frequency increase in the heart rate such as when there is an increase in body stress. It was not known or even expected that the AR-interval can also become longer when the body is subjected to increased stress without simultaneously increasing the heart rate, i.e. the increased cardiac output results essentially from an increase in stroke volume.

The invention utilizes this discovery that increased body stresses alone, without simultaneous increase of the heartbeat frequency also results in a clearly measurable change of the AR-interval which is inversely proportional to the increase in body stress. For example, a shortening of the AR-interval by about 10 milliseconds is equivalent to an additional stress on the body requiring an increase of approximately 10 heartbeats per minute. This is clearly a measurable time variable which can be analyzed using conventional electronic means such as a microprocessor.

The cardiac pacemaker according to the invention maintains the natural synchronization between the atrium and ventricle for a patient's heart so that the patient's heart operates efficiently.

In another embodiment of the invention, the evaluation means is designed so that the operating frequency of the pulse generator is variable between a predetermined minimum stimulation frequency and a predetermined maximum stimulation frequency in accordance with a linear function of the AR-interval. In addition, means are provided to adjust the slope of this linear function to be in accordance with the individual needs of a patient. The evaluation means can also provide circuits to adjust the linear relationship of the operating frequency of the pulse generator on the atrium-ventricle interchange period in accordance with the individual requirements of a patient.

If desired, the evaluation means can be designed so that the operating frequency of the pulse generator is changed according to an S-shaped function between the minimum and maximum stimulation frequencies. This relationship can be determined in accordance with the particular requirements of the patient.

In yet another embodiment of the invention, the evaluation means is designed so that the frequency of the pulse generator is adjusted to the optimal stimulation frequency attributed to a patient's degree of stress. In this circuit arrangement, the regulation of the pulse generator is based on the discovery that when the atrium is stimulated with non-physiologically high stimulation frequencies the AR-interval becomes surprisingly longer and this results in a minimum AR-interval being attributed to each degree of stress to the body. This minimum in AR-interval is reached with each optimal heartbeat frequency.

To utilize this relationship, the evaluating means operates to detect a change in the AR-interval when the operating frequency of the pulse generator is increased. The operating frequency of the pulse generator is reduced when the AR-interval increases. With this control, the operating frequency of the pulse generator is always adjusted to an optimal value essentially equal to the applicable minimum AR-interval.

SUMMARY OF THE DRAWINGS

Examples of embodiments according to the invention are described herein in further detail in connection with the drawings in which.

DESCRIPTION OF THE INVENTION

Figure 1:
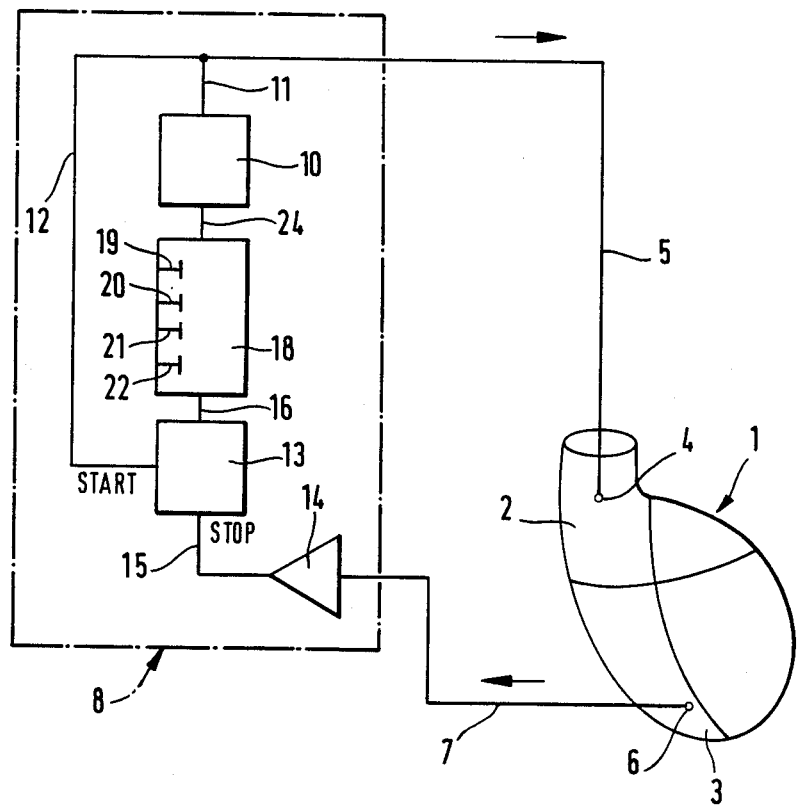
FIG. 1 is a block diagram of a cardiac pacemaker according to the invention.

FIG. 1 shows a block diagram of one embodiment of the invention connected to a heart 1. The atrium 2 of the heart 1 has an atrial stimulation electrode 4 connected or anchored in it and the ventricle 3 of he heart 1 has a ventricle monitoring electrode 6 connected or anchored in it. A pacemaker circuit 8 is connected through line 5 to the stimulation electrode 4 and connected through line 7 to the monitoring electrode 6.

The pacemaker circuit 8 includes a pulse generator 10 which produces electrical pulses connected through line 11 to line 5. The electrical pulses stimulate the atrium 2 through the stimulation electrode 4. The pulse generator 10 is connected through line 12 to a timing circuit 13. The timing circuit 13 is used to measure the AR-interval of the heart 1.

At the time an electrical pulse is communicated to the stimulation electrode 4, the electrical pulse through line 12 initiates the beginning of a time period measurement by the timing circuit 13. An associated excitation signal in the ventricle 3 occurs in response to the electrical pulse in the atrium 2 delivered through the stimulation electrode 4. The excitation signal is detected by the monitoring electrode 6. The excitation signal is coupled through line 7 to an amplifier 14 to provide a signal suitable for providing an input to the timing circuit 13. The signal from the amplifier 14 is coupled through line 15 to the timing circuit 13 and terminates the time period initiated by the electrical pulse from the pulse generator 10.

The time period measured between the electrical pulse signal and the associated excitation signal is proportional to the AR-interval and is coupled through line 16 to an evaluation circuit 18. The evaluation circuit 18 evaluates the measured AR-interval and can change the frequency of the pulse generator 10 through line 24, thereby changing the stimulation frequency.

Figure 2:
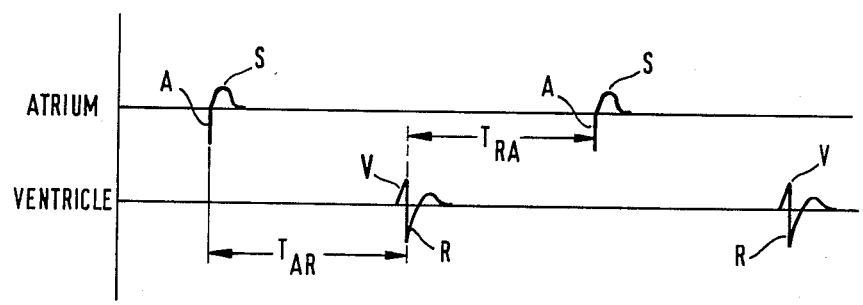
FIG. 2 is a graph in time showing the electrical signals in an atrium and ventricle of the heart.

The graph shown in FIG. 2 shows the sequence of signals in the atrium 2 and the ventricle 3. The vertical axis generally shows amplitude and the horizontal axis is time increasing to the right. The occurrence of an electrical pulse at the stimulation electrode 4 is labelled "A" while the stimulated signal in the atrium 2 is labelled "S". The excitation signal in the ventricle 3 is labelled "V" with the peak of this signal being labeled "R". The time interval between the peak R of the excitation signal V and the next following electrical pulse A is designated as "$T_{RA}$". The duration of the period between two consecutive electrical pulses is equal to $T_{AR} + T_{RA}$. Consequently, the stimulation frequency is:

stimulation frequency $= 1/(T_{AR} + T_{RA}) = F_{St}$

The evaluation circuit 18 shown in FIG. 1 calculates the stimulation frequency "$F_{St}$" according to a predetermined function. For example, the stimulation frequency $F_{St}$ can be taken as linearly related to the $T_{AR}$ according to the following function:

$$F_{St} = -a \times T_{AR} + b$$

In this case, the coefficients "a" and "b" can be selected for an individual patient to optimize the performance of the cardiac pacemaker for that patient. For this purpose, the evaluation circuit 18 has control 19 for the selection of the coefficient "a" and control 20 for the selection of the coefficient "b". Control 21 can be used to set the maximum stimulation frequency while control 22 can be used to set the minimum stimulation frequency. Instead of a linear relationship between the stimulation frequency and the $T_{AR}$, a more complex function having an "S" shape can be used.

Figure 3:
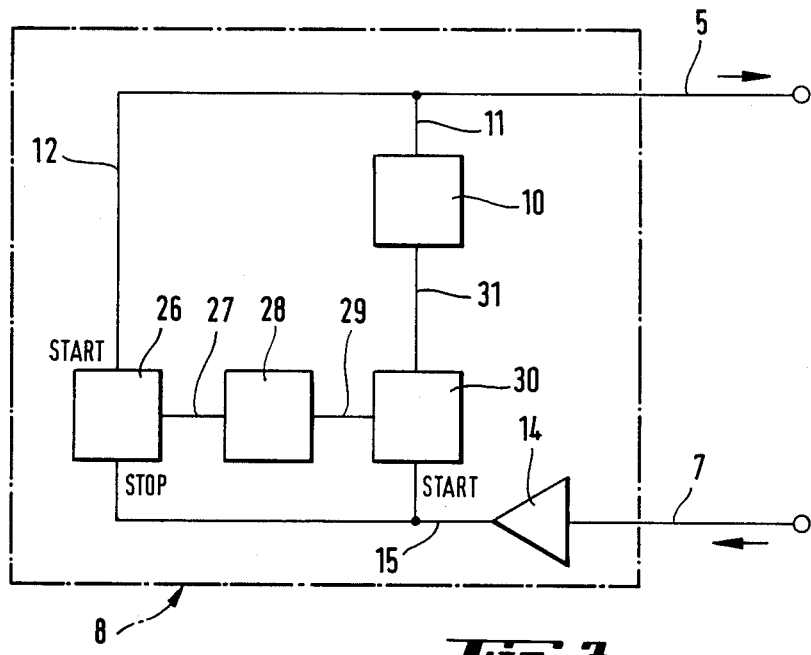
FIG. 3 is a block diagram of an analog control circuit suitable for use in the invention.

FIG. 3 shows a block diagram of a cardiac pacemaker according to the invention using analog technology. The measurement of the time interval $T_{AR}$ is carried out in the following manner. The electrical pulse from the pulse generator 10 is coupled through lines 11 and 12 to the START input of a voltage integrator 26 while the stimulation signal at the monitoring electrode 6 is coupled through line 7 to the amplifier 14. After being amplified, the signal is coupled through line 15 to the STOP input of the voltage integrator 26.

The voltage integrator 26 produces an output voltage proportional to the time interval $T_{AR}$ and this output voltage is coupled through line 27 to an analog function generator 28. The analog function generator 28 computes the time period $T_{RA}$ on the basis of the voltage received and triggers through line 29 a voltage controlled mono flop 30. The mono flop 30 is triggered through its START input by the signal from the amplifier 14, computes a time interval $T_{RA}$ related to the measured AR-interval $T_{AR}$ and triggers the pulse generator 10 through line 31.

Figure 4:
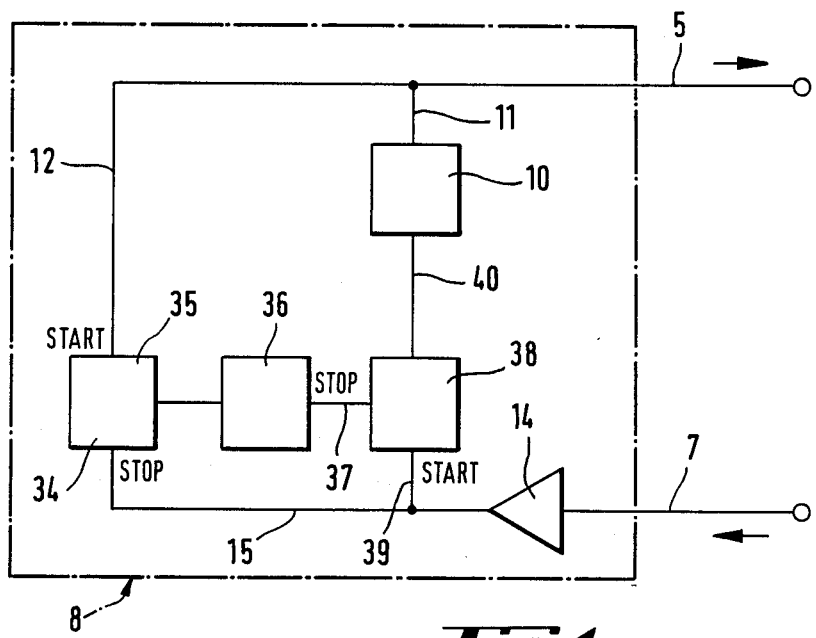
FIG. 4 is a block diagram of a digital control circuit suitable for use in the present invention.

FIG. 4 shows a block diagram of a digital system for the cardiac pacemaker according to the invention. A counter 34 is used for measuring the time interval $T_{AR}$. The START input of the counter 34 is coupled to the pulse generator 10 through lines 11 and 12. An electrical pulse from the pulse generator 10 starts the counter 34. The counting in the counter 34 is interrupted by the signal from the amplifier 14 which is coupled through line 15 to the STOP input of the counter 34. The counter 34 supplies a digital signal corresponding to the time interval $T_{AR}$ through line 35 to the digital function generator 36 which calculates the time $T_{RA}$ corresponding to the digital signal. The STOP input of the counter 38 is triggered by the function generator 36 through line 37. The START input of the counter 38 is connected through line 39 to the output terminal of the amplifier 14.

Through this operation, the counter 38 is started at the peak R of the ventricular signal and the counting process is interrupted subsequently by the function generator 36. The counter 38 triggers the pulse generator 10 through line 40 and ensures the electrical pulses are communicated to the stimulation electrode 4 at the appropriate times, i.e. according to a determined time interval $T_{RA}$ and at a controlled adjustable stimulation frequency.

Figure 5:
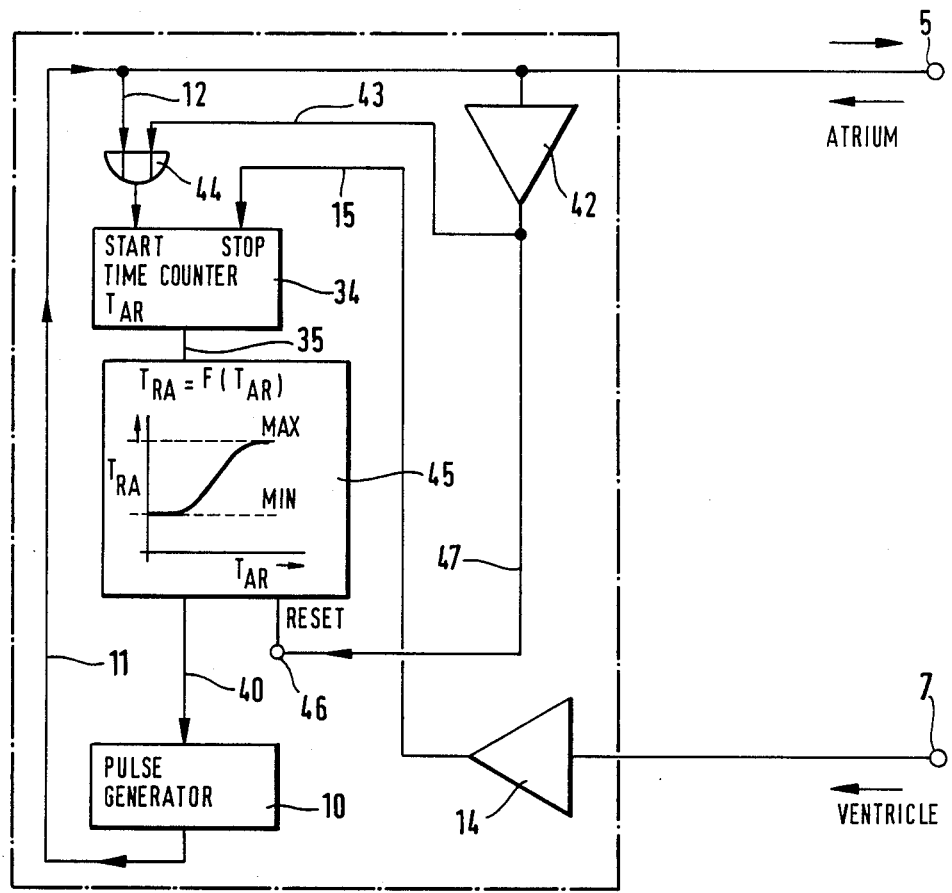
FIG. 5 is a block diagram of a control circuit which can react to the spontaneous activities of an atrium.

FIG. 5 shows a block diagram of another embodiment of the cardiac pacemaker according to the invention. This embodiment includes an additional function in which the stimulation electrode 4 is also used to detect spontaneous activities from which an additional criteria is derived for physiological stimulation.

It is known that with extrasystoles and with tachycardia that the AR-interval ($T_{AR}$) does not become shorter but can even become longer is some cases, up to the point where a total blockage occurs. The occurrence of a spontaneous physiological increase of frequency or a pathological tachycardia can be deduced through the detection of a spontaneous signal in the atrium 2 and the evaluation of the corresponding AR-interval following the occurrence of the spontaneous signal. Thus, the detection of spontaneous activities with the stimulation electrode 4 enables the cardiac pacemaker according to the invention to recognize tachycardia and avoid non-synchronized stimulation during the occurrence of the spontaneous atrial activity. This avoids induced atrial tachycardias or even atrial fibrillation.

Generally, the block diagram in FIG. 5 is similar to the block diagrams shown in FIGS. 3 and 4. FIG. 5 includes a timing circuit in the form of counter 34, a pulse generator 10 and an evaluation circuit in the form of microprocessor 45. The microprocessor 45 controls the frequency of the pulse generator 10 based on the time interval measurements made by the counter 34. The microprocessor 45 can be designed by a person with ordinary skill in the art.

The stimulation electrode 5 in FIG. 5 is coupled to amplifier 42 and OR-gate 44. The OR-gate 44 decouples the output signal from the pulse generator 10 from the output signal of amplifier 42. The pulse generator 10 is coupled through lines 11 and 12 to counter 34 through the OR-gate 44 and the output of the amplifier 42 is coupled through line 43 through the OR-gate 44 to the counter 34. This arrangement isolates the pulse generator 10 and the amplifier 42 from each other.

Whereas the outputs of pulse generator 10 and amplifier 42 are switched to the START input of the counter 34 the STOP input of the counter 34 is coupled through line 15 to the output terminal of the amplifier 14. The signal arriving from the counter 34 and corresponding to the measured AR-interval $T_{AR}$ is coupled through line 35 to the microprocessor 45.

The microprocessor 45 is equipped with a RESET input 46 which is connected through line 47 to the output of the amplifier 42. When a spontaneous activity P occurs, the next following stimulation signal is suppressed and the counter 34 is set back to zero through line 43. As a result, the counter 34 will then measure the time interval $T_{PR}$ beginning with the spontaneous activity P.

Figure 6:
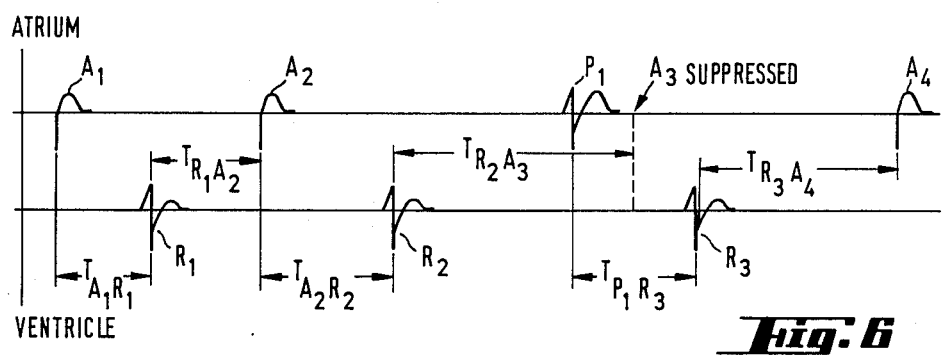
FIG. 6 is a graph showing atrium and ventricle activity in time in response to the control circuit shown in FIG. 5.

FIG. 6 shows graphically the occurrence of spontaneous activities in the heart. The vertical scale is generally amplitude and the horizontal scale is time increasing to the right. FIG. 6 shows in time the occurrence of atrial stimulation signals $A_1$, $A_2$ and $A_4$; an atrial spontaneous activity $P_1$; and the ventricle excitation signals $R_1$, $R_2$ and $R_3$ following $A_1$, $A_2$, and $P_1$, respectively. In particular, FIG. 6 shows that the atrial spontaneous activity $P_1$ has resulted in the suppression of the next stimulation signal $A_3$ and that the AR-interval $T_{P_1R_3}$ is measured starting at this spontaneous activity $P_1$.

The microprocessor 45 computes the time interval $R_{RA}$ from the input signal through line 35 which corresponds to the time interval $T_{AR}$. The calculation of the $T_{RA}$ value is based on data in a memory of the microprocessor 45 and can be a linear approximation. The data is based on the patient. The simple but effective functional correlation between $T_{AR}$ and $T_{RA}$, i.e. of the stimulation frequency, is calculated by finding the corresponding optimal stimulation frequencies of the patient in two defined performance states of the patient. The optimal stimulation frequencies are entered into the microprocessor 45 in the form of two value pairs.

From this, the microprocessor 45 calculates the linear function for the range between the predetermined minimum and maximum stimulation frequencies. The optimal stimulation frequency can be determined by increasing the heartbeat frequency of the patient by means of test stimulation until a minimum $T_{AR}$ has been reached. The correlation between the stimulation frequency and the $T_{AR}$ time is shown schematically in FIG. 7 for three different states of stress.

The microprocessor 45 has an additional role in cases of spontaneous atrial activity of checking to determine if the following $T_{AR}$ time interval is significantly greater than the preceding $T_{AR}$. If a significant increase in time has occurred, the microprocessor 45 initiates an antitachycardial stimulation program after repeated premature spontaneous arterial activities. The command signals from the microprocessor through the pulse generator 10 are through line 40.

Figure 7:
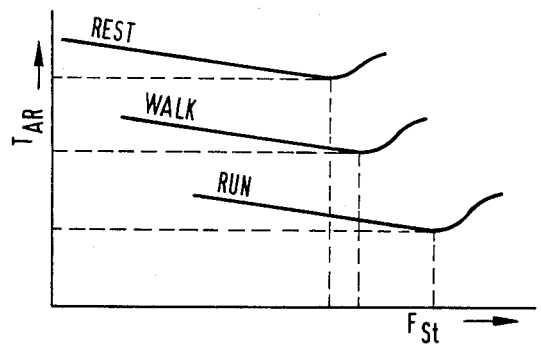
FIG. 7 is a graph showing AR-interval $T_{AR}$ versus stimulation frequency $F_{st}$ for different states of stress.

The microprocessor 45 can also be programmed to provide a stimulation frequency $F_{St}$ corresponding to the optimal stimulation frequency provided for each degree of stress. As shown in FIG. 7, there is an optimal heart frequency for each degree of stress in which the $T_{AR}$ period is at a minimal value. To obtain the stimulation frequency at the optimal stimulation frequency, the microprocessor 45 periodically checks a $T_{AR}$ time to determine if it is correct for the given state of performance.

For this purpose, the stimulation frequency is increased or decreased for one or several time intervals. Thereafter, a control system verifies whether the subsequent AR-interval remains equal to the previous $T_{AR}$ or whether the previous $T_{AR}$ becomes longer or shorter. This allows the minimum of the $T_{AR}$ period to be found so that the stimulation frequency can be controlled in accordance with this minimum time interval.

Figure 8:
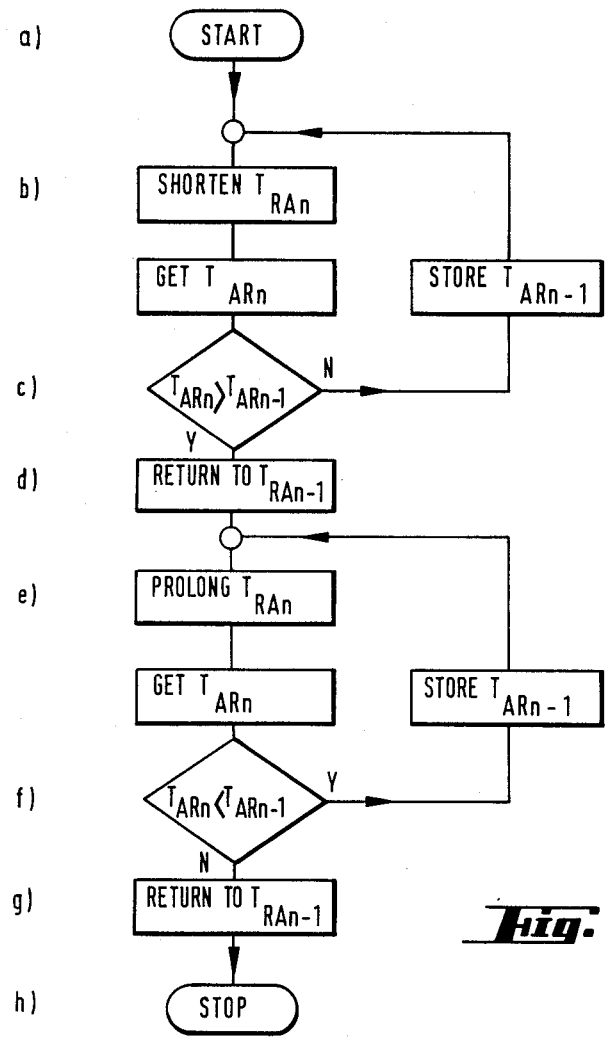
FIG. 8 is a flow diagram for obtaining optimal stimulation frequency for a heart.

FIG. 8 shows a flow diagram of the decision steps for the search to obtain the minimum of the $T_{AR}$ interval as a function of the stimulation frequency or as a function of the $T_{RA}$ interval. The decision steps in FIG. 8 will now be described.

(a) The microprocessor is given the periodic command to store the following intervals of $T_{AR}$ and $T_{RA}$, and to carry out the following operations:

(b) The $T_{AR}$ interval should be shortened.

(c) The n th $T_{AR}$ interval is compared to the preceding (n-1) th $T_{AR}$ interval. If the n th $T_{AR}$ interval is not greater than the preceding $T_{AR}$ interval, the loop is brought back to (b) in order to shorten the $T_{RA}$ interval additionally.

(d) If the n th $T_{AR}$ interval is greater than the preceding $T_{AR}$ interval, the command is given to return to the next-to-last interval. The verification is ended whether or not an AR-interval has been extended as a result of the shortening of the $T_{RA}$ interval.

(e) A command to extend the $T_{RA}$ interval tests if the last $T_{AR}$ interval is smaller than the next-to-last interval.

(f) The n th $T_{AR}$ interval is compared to the preceding (n-1) th $T_{AR}$ interval. If the n th $T_{AR}$ interval is smaller than the preceding $T_{AR}$ interval, then the loop is brought back to (e).

(g) If this is not the case, then the system goes back to the next-to-last $T_{RA}$ interval.

(h) The routine for the control of the optimal $T_{RA}$ interval is ended.

Finally, the above described embodiments of the invention are intended to be illustrative only. Numerous alternative embodiments can be devised by those skilled in the art without departing from the spirit and the scope of the following claims.

I claim:

1. A cardiac pacemaker having a variable stimulation frequency comprising,
    a stimulation electrode for delivering electrical stimulation pulses at a stimulation frequency to an atrium of a heart of a patient,
    a pulse generator coupled to said stimulation electrode for producing said electrical pulses at said stimulation frequency,
    a monitoring electrode for sensing excitation signals in a ventricle of said heart in response to said electrical stimulation pulses delivered to said atrium,
    timing means for measuring the AR time intervals ($T_{AR}$) between the electrical stimulation pulses and said excitation signals of said ventricle, and
    processing means for controlling the stimulation frequency of said pulse generator to adjust said stimulation frequency in response to the measured AR intervals in accordance with a control function which linearly correlates a decreasing AR interval with an increasing stimulation rate.

2. The pacemaker of claim 1 wherein aid processing means is a microprocessor.

3. The pacemaker of claim 1 wherein said stimulation frequency is limited by predetermined minimum and maximum stimulation frequencies.

4. The pacemaker of claim 1 wherein said pulse generator is inhibited under control of said processing means in response to a spontaneous atrial beat.

5. A cardiac pacemaker having a variable stimulation frequency comprising,
    a stimulation electrode for delivering electrical stimulation pulses at a stimulation frequency to an atrium of a heart of a patient,
    a pulse generator coupled to said stimulation electrode for producing said electrical pulses at said stimulation frequency,
    a monitoring electrode for sensing excitation signals in a ventricle of said heart in response to said electrical stimulation pulses delivered to said atrium,
    timing means for measuring the AR time intervals ($T_{AR}$) between the electrical stimulation pulses and said excitation signals of said ventricle, and
    processing means for controlling the stimulation frequency of the pulse generator to adjust said stimulation frequency in response to the measured AR intervals in accordance with a control function which linearly correlates a decreasing AR interval with an increasing stimulation rate,
    wherein said processing means is a microprocessor, and
    wherein the stimulation frequency ($F_{st}$) is related to the AR time interval ($T_{AR}$) in accordance with the control function $$F_{st} = -a \cdot T_{AR} + b$$

where a and b are parameters determined individually for the heart of each patient, said control function being evaluated by said microprocessor in response to said measurement of ($T_{AR}$).

6. A cardiac pacemaker having a variable stimulation frequency comprising a stimulation electrode for delivering electrical stimulation pulses at a stimulation frequency to an atrium of a heart of a patient, a pulse generator coupled to said stimulation electrode for producing said electrical pulses at said stimulation frequency, a monitoring electrode for sensing excitation signals in a ventricle of said heart in response to said electrical stimulation pulses delivered to said atrium, timing means for measuring the AR time intervals between the electrical stimulation pulses and said excitation signals of said ventricle, and processing means for controlling the stimulation frequency of said pulse generator in response to said timing means to maintain said AR interval at a minimal value for a particular level of exercise for the patient.

* * * * *